US008630995B2

(12) United States Patent
Bachert et al.

(10) Patent No.: US 8,630,995 B2
(45) Date of Patent: Jan. 14, 2014

(54) METHODS AND SYSTEMS FOR ACQUIRING AND PROCESSING VETERINARY-RELATED INFORMATION TO FACILITATE DIFFERENTIAL DIAGNOSIS

(76) Inventors: Raymond William Bachert, Woodinville, WA (US); Molly Kathleen Bachert, Woodinville, WA (US)

( * ) Notice: Subject to any disclaimer, the term of this patent is extended or adjusted under 35 U.S.C. 154(b) by 343 days.

(21) Appl. No.: 13/234,165

(22) Filed: Sep. 16, 2011

(65) Prior Publication Data
US 2013/0073554 A1    Mar. 21, 2013

(51) Int. Cl.
*G06F 17/30* (2006.01)
(52) U.S. Cl.
USPC ............................ 707/709; 707/738; 707/794
(58) Field of Classification Search
USPC .................... 707/709, 738, 794, 755
See application file for complete search history.

(56) References Cited

U.S. PATENT DOCUMENTS

| 6,397,190 | B1 * | 5/2002 | Goetz ............................... 705/3 |
| 8,452,670 | B2 * | 5/2013 | Sutter et al. ................... 705/27.1 |
| 2006/0074718 | A1 * | 4/2006 | Fucci et al. ....................... 705/3 |
| 2010/0256991 | A1 | 10/2010 | Ishikawa et al. |
| 2011/0022479 | A1 * | 1/2011 | Henley ......................... 705/14.73 |
| 2011/0196804 | A1 * | 8/2011 | Sutter et al. .................... 705/332 |
| 2011/0199390 | A1 | 8/2011 | Iizuka et al. |
| 2012/0265702 | A1 * | 10/2012 | Maher ........................... 705/317 |

* cited by examiner

*Primary Examiner* — Cheryl Lewis

(57) ABSTRACT

Computer-implemented methods and systems for acquiring and processing veterinary-related information, such as non-human animal diseases, associated medical signs, differentials, and treatment-related information, are provided. The disclosed methods and systems facilitate performing computer-based differential diagnosis by veterinary medicine practitioners. An example method may comprise: importing veterinary-related text information, wherein the veterinary-related text information is related to one or more non-human animal diseases; parsing the veterinary-related text information into one or more terms; determining relations between the one or more terms; classifying the one or more terms such that each term relates to one of: a non-human animal species, an animal disease, a medical sign and a treatment; and generating a database table associated with the imported veterinary-related text information, the database table comprising the one or more classified terms and the relations therebetween.

20 Claims, 8 Drawing Sheets

FIG. 6

METHODS AND SYSTEMS FOR ACQUIRING AND PROCESSING VETERINARY-RELATED INFORMATION TO FACILITATE DIFFERENTIAL DIAGNOSIS

TECHNICAL FIELD

This disclosure relates generally to data processing, and more particularly to computer-implemented methods and systems for acquiring and processing veterinary-related information. The disclosed methods and systems facilitate performing computer-based differential diagnosis for veterinary medicine practitioners.

DESCRIPTION OF RELATED ART

The approaches described in this section could be pursued but are not necessarily approaches that have been previously conceived or pursued. Therefore, unless otherwise indicated, it should not be assumed that any of the approaches described in this section qualify as prior art merely by virtue of their inclusion in this section.

Although computer-based medical decision support for diagnosing human illnesses has evolved significantly, diagnosis and treatment of animals by veterinary medicine practitioners can still extensively depend on the knowledge and skill of the practitioners. When a practitioner does not improve their knowledge on a continual basis, animals under that practitioner's care may not receive the best diagnostics or treatments. Unfortunately, the more time a practitioner spends in researching the state of veterinary medicine to treat a particular animal, the less time the practitioner has to spend with animals and their handlers.

When diagnosing animals, practitioners can use practice management software or save information in case files, but they can generally only get cooperation from other practitioners in the same hospital if records are shared. To share records otherwise, numerous phone calls and faxes are generally required, which can also take the practitioner's time away from the patient and client. In some cases, the practitioners may make posts on online forums or other resources to share their experience. However, search over such online resources by other practitioners may require a significant amount of time to find required information.

Moreover, determining a medical diagnosis for non-human animals is often a difficult task. An animal cannot talk to describe their symptoms and practitioners are limited to objective medical signs detected during examinations. It is often difficult for veterinary practitioners to determine a certain disease based on the combination of obtained animal clinical signs or characteristics.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In accordance with various embodiments and the corresponding disclosure thereof, a computer-implemented method for acquiring and processing information about non-human animal diseases is provided. The method may comprise: importing veterinary-related text information, wherein the veterinary-related text information is related to one or more non-human animal diseases; parsing the veterinary-related text information into one or more terms; determining relations between the one or more terms; classifying the one or more terms such that each term relates to one of: a non-human animal species, an animal disease, a medical sign and a treatment; and generating a database table associated with the imported veterinary-related text information, the database table comprising the one or more of classified terms and the relations therebetween.

In one example embodiment, the method may further comprise selecting at least one predetermined ontology associated with the one or more terms, wherein the ontology has a structural framework of terms and relations therebetween. The determining relations between the one or more terms can be based on the structural framework of the at least one ontology. The classifying of the one or more terms can be based on the structural framework of the at least one ontology. The parsing of the veterinary-related text information may comprise applying predetermined semantic rules.

In yet another example embodiment, the method may further comprise assigning weight factors to the terms associated with the veterinary-related text information; and storing the weight factors in the database table. The generating the database table associated with the imported veterinary-related text information may comprise updating an existing database table. The method may further comprise crawling one or more resources over a network to import the veterinary-related text information. The method may further comprise generating, upon a user request, a web page related to a non-human animal disease, the web page comprising one or more of medical signs and treatments acquired from multiple resources. The method may further comprise receiving a user request to conduct a veterinary differential diagnosis, wherein the user request comprises one or more of preselected medical signs; searching for information about non-human animal diseases, associated with the preselected medical signs, through the one or more database tables; and reporting the list of one or more non-human animal diseases.

The method may further comprise ranking the list of one or more non-human animal diseases based on the weight factors applied to the terms; and sorting the one or more non-human animal diseases on their relevancy. The method may further comprise providing a user interface to access, search over, and process information about non-human animal diseases among the at least one database table. The method may further comprise virtually linking the generated database table associated with the imported veterinary-related text information with one or more remote resources in the network.

According to yet more various embodiments, a system for acquiring and processing information about non-human animal diseases is provided. The system may comprise: a communication module configured to import veterinary-related text information, wherein the veterinary-related text information comprises information related to one or more non-human animal diseases; a parsing module configured to parse the veterinary-related text information into one or more terms; a relationship determination module configured to determine relations between the one or more terms; a classifying module configured to classify the one or more terms such that each term relates to one of: a non-human animal species, an animal disease, a medical sign and a treatment; and a database table generator configured to generate a database table associated with the imported veterinary-related text information, the database table comprising the one or more of classified terms and the relations therebetween.

In one example embodiment, the system may further comprise an ontology selecting module configured to select at least one predetermined ontology associated with the one or more terms, wherein the ontology has a structural framework of terms and relations therebetween. The system may further comprise a ranking module configured to assign weight factors to the terms associated with the veterinary-related text information, and rank the list of one or more non-human animal diseases based on the weight factors applied to the terms. The system may further comprise a crawling module configured to crawl one or more resources over a network to import the veterinary-related text information. The system may further comprise a web page generator configured to generate, upon a user request, a web page related to a non-human animal disease, the web page comprising one or more of medical signs and treatments acquired from multiple resources. The system may further comprise a user interface configured to enable users to access, search over, and process information about non-human animal diseases among the at least one database table.

According to yet more various embodiments, a computer-readable medium having instructions stored thereon, which, when executed by one or more computers, cause the one or more computers to: import veterinary-related text information, wherein the veterinary-related text information is related to one or more non-human animal diseases; parse the veterinary-related text information into one or more terms; determine relations between the one or more terms; classify the one or more terms such that each term relates to one of: a non-human animal species, an animal disease, a medical sign and a treatment; and generate a database table associated with the imported veterinary-related text information, the database table comprising the one or more of classified terms and the relations therebetween.

To the accomplishment of the foregoing and related ends, the one or more aspects comprise the features hereinafter fully described and particularly pointed out in the claims. The following description and the drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

Embodiments are illustrated by way of example and not limitation in the figures of the accompanying drawings, in which like references indicate similar elements and in which:

FIG. 6 is a simplified illustration of a graphical user interface of a web page for showing search results based on pre-selected one or more medical signs according to an example embodiment.

DETAILED DESCRIPTION

Figure 1:
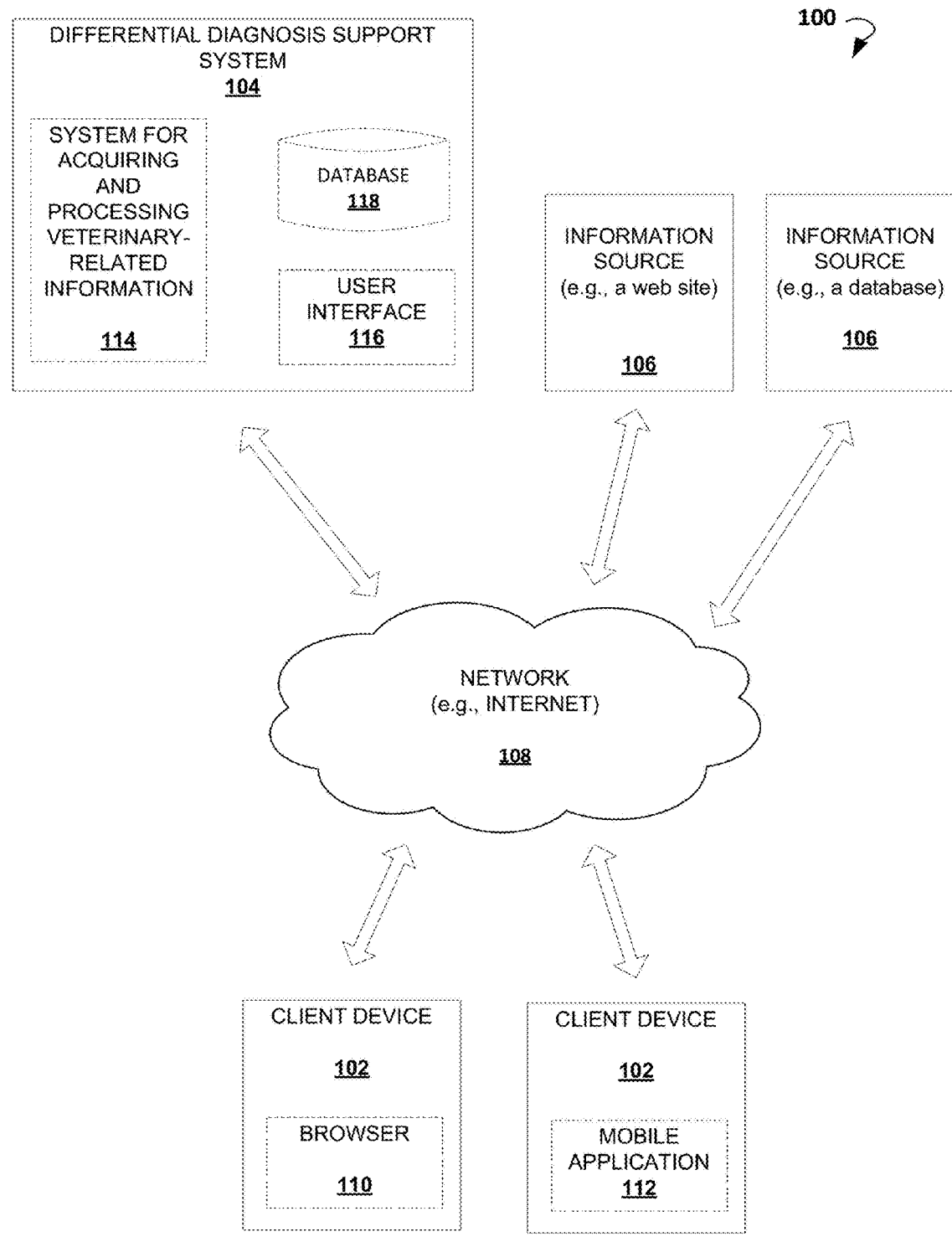
FIG. 1 shows a block diagram illustrating a system environment suitable for acquiring and processing veterinary-related information to facilitate differential diagnosis according to an example embodiment.

The following detailed description includes references to the accompanying drawings, which form a part of the detailed description. The drawings show illustrations in accordance with example embodiments. These example embodiments, which are also referred to herein as "examples" are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

In this document, the terms "a" or "an" are used, as is common in patent documents, to include one or more than one. In this document, the term "or" is used to refer to a nonexclusive "or", such that "A or B" includes "A but not B", "B but not A", and "A and B", unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The embodiments described herein relate to computer-implemented methods and systems for acquiring and processing veterinary-related information to facilitate differential diagnosis of non-human animals. The veterinary-related information may refer to non-human animal diseases, associated medical signs, differentials, and treatment-related information.

Differential diagnosis is a method to identify a certain disease on the basis of available symptoms, medical signs, detected characteristics, previous illness history, etc. This method often involves first making a list of possible diagnoses, then attempting to remove diagnoses from the list until one diagnosis remains. In some cases, there will remain no diagnosis, which may suggest a veterinary practitioner has made an error, or that the true diagnosis is unknown to medicine. Removing diagnoses from the list is done by making observations and using tests that should have different results, depending on which diagnosis is correct.

According to various embodiments disclosed herein, veterinary practitioners may utilize a differential diagnosis support system to support making diagnostic decisions. Such system may be implemented as software embedded in a computing environment. In general, the differential diagnosis support system allows the veterinary practitioners to generate search requests comprising data obtained upon animal examination, and responsive to these search requests, the practitioners are provided with a list of animal diseases that are somehow associated with the examination data. The veterinary practitioners may then review descriptions of found diseases including medical signs data, treatment information, description of past cases, specialist discussions, and other content, thereby providing quick decision support. The system may also provide the practitioners with a useful tool to share their experience among other system users, to create or update existing disease descriptions, treatments methods, outcomes, etc.

According to various embodiments, the differential diagnosis support system may have a database to store veterinary-related information. The veterinary-related information may comprise, among other things, descriptions of animal diseases, associated with them medical signs, relationships therebetween, treatment information, and descriptions of real cases. The database may be updated with new database tables, each being related to a certain animal disease. The database tables may be generated and updated by users or automatically by the differential diagnosis support system.

According to various embodiments, the differential diagnosis support system can be configured to populate the database with new information from multiple remote online resources. More specifically, the differential diagnosis support system may comprise a system for acquiring and processing the veterinary-related information. Such system may crawl the Internet or any other network to retrieve information related to certain diseases. For example, the system may import articles or online publications (e.g., PubMed articles) related to certain animal diseases, following keywords used therein. The importing can be performed on an ongoing basis. The imported text information is then parsed into sentences using, for example, an open source semantic processing library. At the next step, the terms are extracted from the sentences.

The system may comprise multiple computer ontologies defining terms and relationships therebetween related to a certain field or disease. The extracted terms can be matched to these ontologies such that the terms are separated into known and unknown terms. The unknown terms can be determined by mapping to one or more computer ontologies. The system may also determine relationships between the extracted terms.

Based on the analysis of terms and their relations, the system classifies the terms such that each term relates to one of: a non-human animal species, an animal disease, a medical sign, a differential, and a treatment. The terms may also be assigned with weight factors, which may represent their relevancy for a specific subject or disease. The relevancy can be determined based on "citation index".

The system may then generate a database table associated with the imported veterinary-related text information. The database table may comprise the classified terms, the relations therebetween, and a virtual link to the online resource or publication comprising the imported veterinary-related text information.

According to various examples, the system may then uniquely generate web pages related to the database tables. The system may also comprise a user interface to interact with the system. The user interface can be used to search for information over the system database tables. Users may search for description of animal diseases directly by generating a user request comprising a disease name or they may input one or more medical signs obtained during examination to get a list of possible diseases possessing the same medical signs. Accordingly, the generated web pages related to animal diseases may comprise information related to description of diseases, medical signs, treatment-related information, description of cases, practitioner advices or discussions, links to external resources, and so forth. Lists of possible animal diseases generated responsive to the user request may optionally be sorted or ranked based on the weight factors assigned to them. Since the system is accessible over a network, such as the Internet, their advantages can be used by many practitioners without requiring them to be in the same practice management software system.

The disclosed approaches for acquiring and processing the veterinary-related information are significantly faster and more relevant than prior art methods of diagnosing veterinary patients. In contrast to prior art systems for sharing the veterinary-related information, such as online forums, the disclosed technology enables veterinarian practitioners to search for multiple clinical signs at once and then to view resulting differentials diagnoses based on relationship building software. The disclosed approaches also enable a practitioner to start a new case online and then send that case to specialists for evaluation. Accordingly, the disclosed methods and systems are a very useful and unique tool to facilitate computer-based differential diagnosis of non-human animals.

The following description provides the detailed description of various embodiments related to methods and systems for acquiring and processing the veterinary-related information.

Referring now to the drawings, FIG. 1 shows a block diagram illustrating a system environment 100 suitable for acquiring and processing the veterinary-related information to facilitate differential diagnosis according to an example embodiment.

The system environment 100 comprises one or more client devices 102, a differential diagnosis support system 104, one or more information sources 106, and a network 108. The network 108 may couple the aforementioned modules.

The network 108 is a network of data processing nodes interconnected for the purpose of data communication, which may be utilized to communicatively couple various components of the environment 100. The network 108 may include the Internet or any other network capable of communicating data between devices. Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port, such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 108 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection, mesh or Digi® networking.

As used herein, the term "client device" refers to a computer, a laptop, a tablet computer, a portable computing device, a personal digital assistant (PDA), a handheld cellular phone, a mobile phone, a smart phone, a handheld device having wireless connection capability, or any other electronic device suitable for communicating data via the network 108.

The client devices 102 may be configured to browse web sites or access remote servers via the network 108. For example, the client devices 102 can be used to communicate with the differential diagnosis support system 104. In some embodiments, the client devices 102 may comprise a browser 110 providing the ability to browse and interact with sites on the Internet. In yet more embodiments, the client devices 102 may embed ad hoc software, e.g. a mobile application 112 providing the ability to communicate with the differential diagnosis support system 104.

The differential diagnosis support system 104 can be implemented as a remote server having multiple modules and databases accessible over the network 108. In particular, the differential diagnosis support system 104 may comprise, among other things, a system 114 for acquiring and processing veterinary-related information, a user interface 116, and one or more databases 118 to store the veterinary-related information and any other relevant information or software codes. The remote server may optionally host a website to enable users access the one or more database 118 via the user interface 116.

The system 114 for acquiring and processing veterinary-related information is described in detail below with reference to FIG. 2.

According to various embodiments disclosed herein, the one or more information sources 106 may include any web page on the Internet, which comprise any veterinary-related information. In one example, the information source 106 is a web server hosting multiple medicine publications (e.g., "PubMed"). In yet another example, the information source 106 is a database accessible over the network 108.

Figure 2:
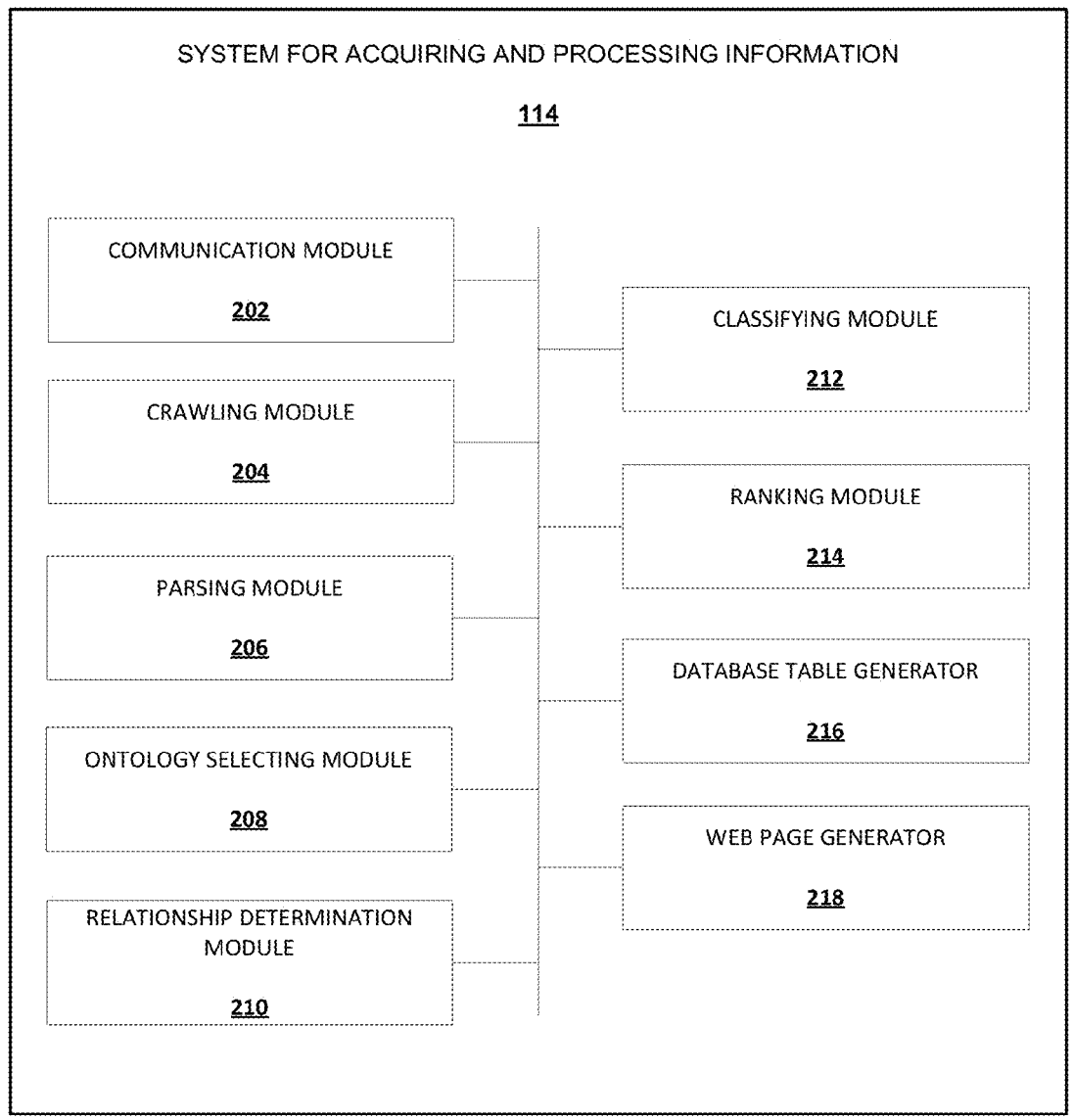
FIG. 2 is a diagram of a system for acquiring and processing veterinary-related information according to an example embodiment.

FIG. 2 is a diagram of the system 114 for acquiring and processing veterinary-related information according to an example embodiment. In this embodiment, the system 114 for acquiring and processing veterinary-related information may include a communication module 202, a crawling module 204, a parsing module 206, an ontology selecting module 208, a relationship determination module 210, a classifying module 212, a ranking module 214, a database table generator 216, and a web page generator 218.

In other embodiments, the system 114 for acquiring and processing veterinary-related information may include additional, fewer, or different modules for various applications. Furthermore, all modules can be integrated within a single apparatus, or, alternatively, can be remotely located and optionally be accessed via a third party.

The system 114 for acquiring and processing veterinary-related information may be implemented as hardware having software installed thereon that implements any steps necessary to operate the system 114 according to various embodiments disclosed herein.

The communication module 202 may be configured to receive different user requests, such as requests to conduct differential diagnosis to retrieve certain information from the database 118. The communication module 202 may also be configured to exchange data between the remote information sources 106 or other modules within the differential diagnosis support system 104. In certain embodiments, the communication module 202 may be configured to import information from the one or more remote information sources 106. The imported information can be stored in the database 118.

The crawling module 204 can be configured to craw the one or more remote information sources 106 to search for certain online publications. The search can be performed based on specific keywords within a specific field. The crawling can be automatic or initiated by users.

The parsing module 206 can be configured to parse the imported veterinary-related information into sentences. In one example, Open Natural Language Processing Libraries can be used to parse a text into sentences, following certain semantic rules. The parsed sentences can be saved in the database 118 with a link to the imported veterinary-related information.

The parsing module 206 can be configured to extract terms from the sentences. It should be noted that in some alternative examples, the parsing module 206 may parse the terms directly along with parsing the text into sentences. Those skilled in the art would understand that any applicable method for parsing texts can be used.

The ontology selecting module 208 can be configured to select at least one predetermined computer ontology associated with the one or more terms. The computer ontologies comprise structural frameworks of multiple terms and relations therebetween. The ontology terms may include the terms related to animal breeds, animal species, animal diseases, bacteria, anatomical terms, insects, plants, drugs, etc. The computer ontologies may be used by the system 114 to interpret the terms and relationships between them, as will be described below.

The relationship determination module 210 can be configured to determine relations between the one or more terms extracted/parsed from the veterinary-related text information. The relationships may refer to a relationship "IS/ARE", a relationship "HAVE/HAS", and a relationship "GROUP". In other words, the relationships determine how two or more terms are interrelated with each other.

In one example, the phrase "broken tibia" can be analyzed. There are two terms, i.e. "broken" and "tibia". The relationship determination module 210 can determine that here the relationship "IS" is used such that it is meant "tibia is broken".

In one other example, the relationship "HAS" is used in the following phrase "A dog has a tail".

At last, the relationship "GROUP" is used for nouns that can be grouped. For example, from the phrase "Dogs have tails, ears and fur" it follows that "tails, ears and fur" is a "Group".

The classifying module 212 can be configured to classify the one or more parsed/extracted terms. For instance, the terms can be classified in such a way that each of them relates to one of the following: a non-human animal species, an animal disease, a medical sign, a differential, and a treatment. The classification process can be based on the selected computer ontology.

The ranking module 214 can be configured to assign weight factors to the terms. The weight factors in turn can be selected or pre-calculated depending on multiple factors, such as a citation frequency (citation index) of a certain term, an algorithm used in the selected computer ontology, a distance between certain terms in the text, etc. The ranking module 214 thus facilitates (or may conduct) sorting of search results based on the weight factors.

The database table generator 216 can be configured to generate a database table. The database table may comprise all classified terms, the relationships therebetween, the weight factors, the imported veterinary-related text information and/or a link to an external information source having such information.

The web page generator 218 can be configured to generate web pages either automatically, or upon a user request. In one example, the web page may relate to an animal disease and may comprise its description, one or more medical signs, treatments, descriptions of multiple cases, related posts and publication, links to remote information sources, and so forth. In one another example, the web page may be generated responsive to the user request, which may have one or more medical signs peculiar to an examined animal. In other words, it is the user request to perform computer-based differential diagnosis. In this case, the web page may comprise a list of animal diseases associated with the medical signs contained in the user request. The animal diseases listings may be sorted according to one or more methods, e.g. in line with the assigned weight factors. Moreover, each animal disease listing may be clickable to enable users to get more information related to the selectable disease.

Figure 3:
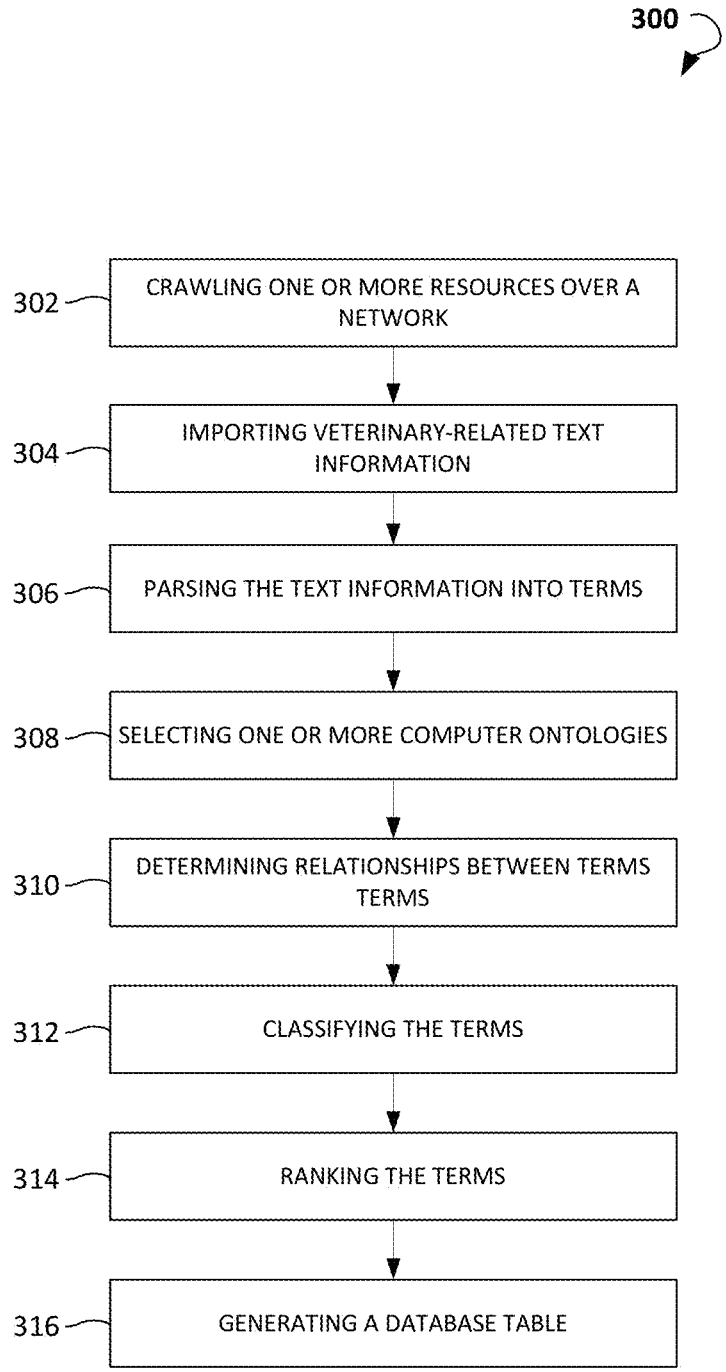
FIG. 3 is a process flow diagram showing a method for acquiring and processing veterinary-related information according to an example embodiment.

FIG. 3 is a process flow diagram showing a method 300 for acquiring and processing veterinary-related information according to an example embodiment. The method 300 may be performed by processing logic that may comprise hardware (e.g., dedicated logic, programmable logic, and microcode), software (such as software run on a general-purpose computer system or a dedicated machine), or a combination of both. In one example embodiment, the processing logic resides at the system 114 for acquiring and processing veterinary-related information or the differential diagnosis support system 104.

The method 300 can be performed by various modules discussed above with reference to FIG. 2. Each of these modules can comprise processing logic. It will be appreciated by one of ordinary skill that examples of the foregoing modules may be virtual, and instructions said to be executed by a module may, in fact, be retrieved and executed by a processor. The foregoing modules may also include memory cards, servers, and/or computer disks. Although various modules may be configured to perform some or all of various steps described herein, fewer or more modules may be provided and still fall within the scope of various embodiments.

As shown in FIG. 3, the method 300 may commence at operation 302 with the crawling module 204 crawling network resources, such as the information sources 106, which can be external web sites or databases. The crawling can be based on pre-selected keywords or publication dates. The found relevant online publication(s) is(are) imported to the system 114 at operation 304.

At operation 306, the parsing module 206 performs parsing the imported online publication (or "veterinary-related text information" as mentioned above) into sentences and terms.

At operation 308, the ontology selecting module 208 selects one or more computer ontologies related to the extracted terms. The computer ontologies may comprise structural frameworks of multiple terms and relations therebetween. The ontology terms may include such terms related to animal breeds, animal species, animal diseases, bacteria, anatomical terms, insects, plants, drugs, etc.

At operation 310, the relationship determination module 210 determines relationships between the extracted terms. This process may be optionally based on the structural framework of pre-selected ontology.

At operation 312, the classifying module 212 classifies the extracted terms to relate each of them to a certain category. In one embodiment, the terms may be classified within the following concepts: a non-human animal species, an animal disease, a medical sign, a differential, and a treatment. The classification process can be based on the selected computer ontology.

At operation 314, the ranking module 214 may optionally assign weight factors to the extracted terms. This procedure facilitates further ranking or sorting search results to list the most relevant clinical signs in the first place.

At operation 316, the database table generator 216 generates a database table which may comprise all classified terms, the relationships therebetween, the weight factors, the imported veterinary-related text information and/or a link to an external information source having such information.

Figure 4:
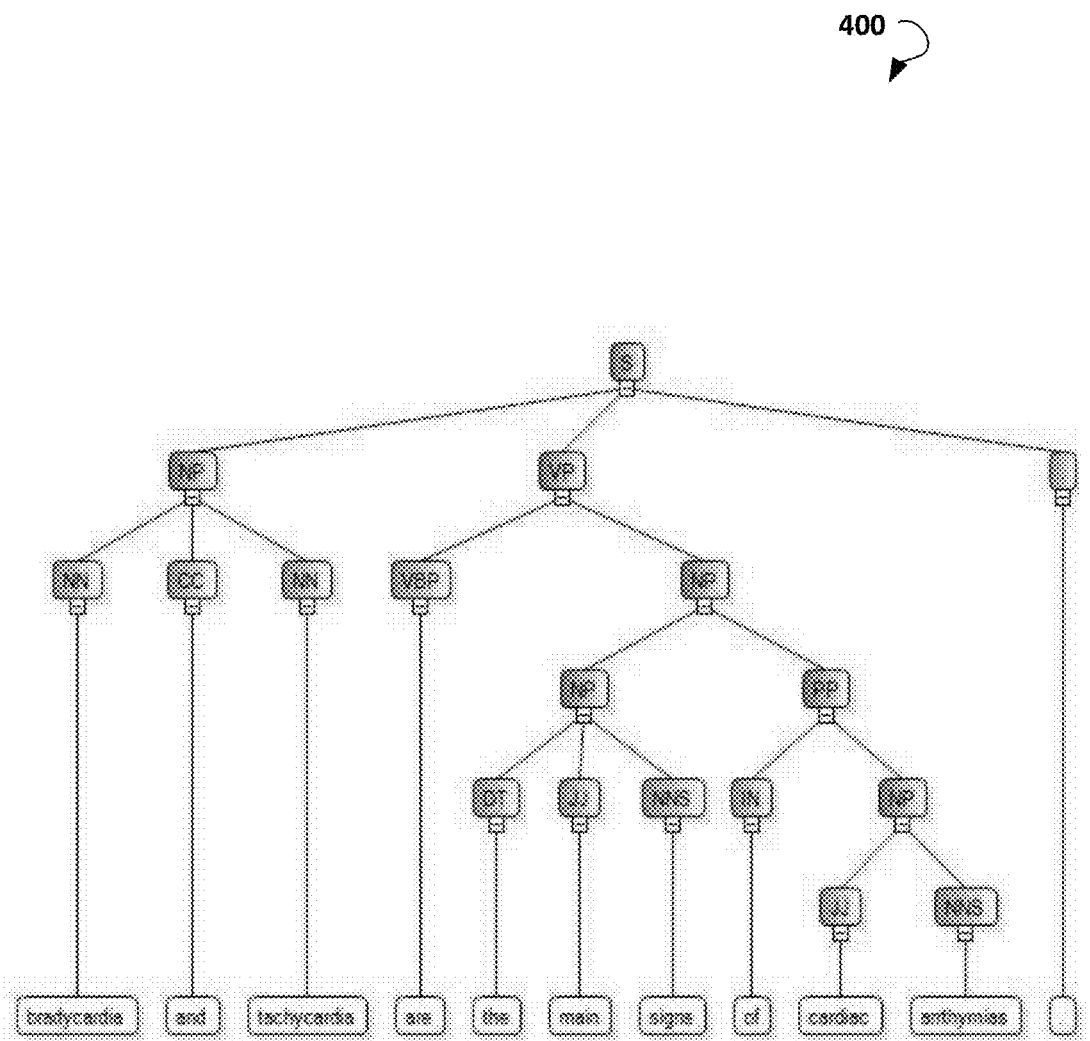
FIG. 4 is an illustration of parsing and relationship generating processes according to an example embodiment.

FIG. 4 is an illustration of parsing and relationship generating processes according to an example embodiment.

Assume the system 114 for acquiring and processing veterinary-related information imported a text and the following sentence was extracted and parsed: "Bradycardia and tachycardia are the main signs of cardiac arrhythmia".

According to the method as described with reference to FIG. 3, the extracted sentence is broken into multiple terms. This process of breaking terms is illustrated in FIG. 4. The selected computer ontology is used to classify each term and generate relations between them. For example:

"Bradycardia" and "Tachycardia" are grouped together in the sentence as a noun phrase (NP). The word starts a "GROUP" relationship between these terms.

"Are" starts a "IS A" relationship with the plural noun (NNS) "signs".

"Signs" has a predefined relationship to "IS" a "clinical sign".

"Of" starts a "HAS" relationship with the noun phrase "Cardiac Arrhythmias".

Following this example, the logic of determining and assigning relationships can be extended as follows:

If "Bradycardia and Tachycardia" is a group and IS a sign, then separately, the terms bradycardia is a sign and tachycardia is a sign.

"Bradycardia" is a clinical sign (""signs" is a clinical sign" is a known relationship).

"Tachycardia" is a clinical sign.

Since differentials "HAVE/HAS" relationship with clinical signs (known relationship), and "bradycardia" and "tachycardia" (are signs) and "HAVE/HAS" relationship with "cardiac arrhythmias", we can imply that "cardiac arrhythmias" is a differential.

The determined relationships are then stored in a corresponding database table associated with the imported veterinary-related text information.

According to various embodiments, some terms upon extraction from sentences may not be classified. In other words, some terms can be considered "unknown". If this is the case, such terms can be further verified and/or defined by system operators. In some embodiments, unknown terms can be subjected to a morphological analysis. For example, if the term "Hyperkalemia" used in the phrase "One of the first indicators of heart disease are bradycardia, hyperkalemia and tachycardia" is considered unknown, it can be determined whether the term comprises Latin roots. In this example, the Latin root is "Hyper" which means "increase in". Following such analysis, the entire term "Hyperkalemia" can be related to a clinical sign.

Figure 5:
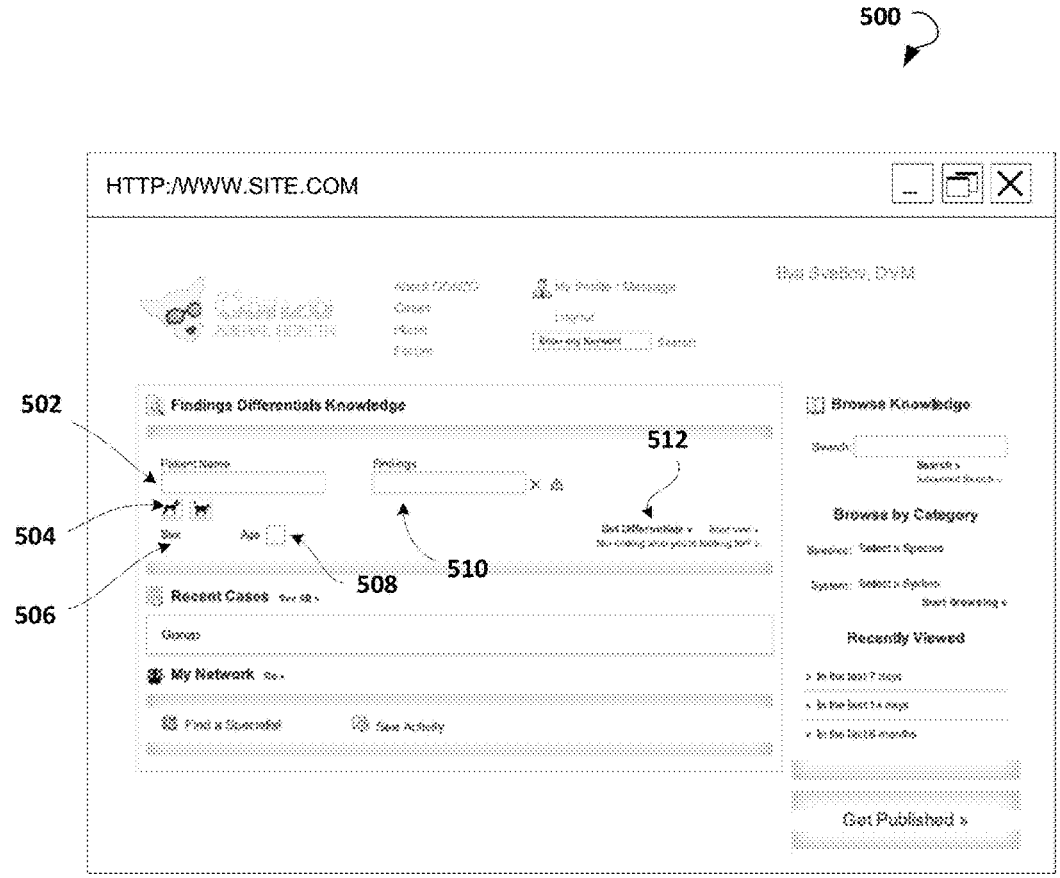
FIG. 5 is a simplified illustration of a graphical user interface of a web page for conducting a computer-based differential diagnosis related to non-human animals according to an example embodiment.

FIG. 5 is a simplified illustration of a graphical user interface 500 of a web page for conducting a computer-based differential diagnosis related to non-human animals according to an example embodiment. The graphical user interface 500 may be represented as a window (e.g., a browser window) to show its content. The graphical user interface 500 may be presented on a screen of the client device 102 via the browser 110.

By way of example and not limitation, the graphical user interface 500 shows a search tool to define medical signs obtained during animal examination. The graphical user interface 500 may comprise a widget 502 to define a patient name, a widget 504 to indicate a species, a widget 506 to indicate a patient sex, a widget 508 to indicate a patient age, a widget 510 to select one or more medical signs, and a widget 512 to initiate a search process.

The widgets 502 to 512 can be represented as one or more of actionable buttons, radio buttons, cycle buttons, controls, icons, hyperlinks, text boxes, list boxes, check boxes, etc.

The widget 512 to initiate a search process can initiate the search over the database 118 to list one or more animal diseases which are characterized by the indicated medical signs.

Figure 6:
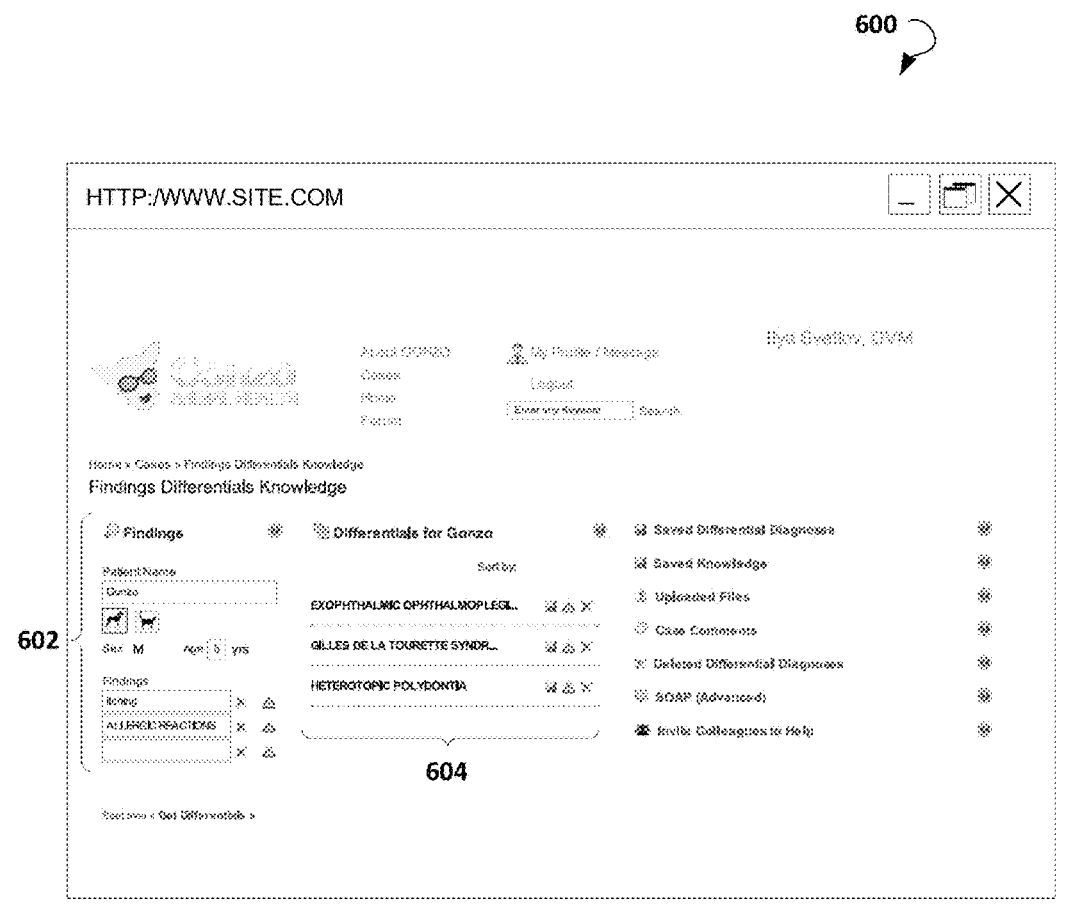

FIG. 6 is a simplified illustration of a graphical user interface 600 of a web page for showing search results based on pre-selected one or more medical signs according to an example embodiment. The graphical user interface 600 may be represented as a window (e.g., a browser window) to show its content. The graphical user interface 600 may be presented on a screen of the client device 102 via the browser 110.

By way of example and not limitation, the graphical user interface 600 may comprise a section 602 showing clinical signs as preset by a user. Specifically, the section 602 may comprise the widget 502 to define a patient name, the widget 504 to indicate a species, the widget 506 to indicate a patient sex, the widget 508 to indicate a patient age, the widget 510 to select one or more medical signs, and the widget 512 to start over a search process.

The graphical user interface 600 may also comprise a section 604 showing the results of the search, i.e. a list of animal diseases which has characteristics associated with the indicated clinical signs. Each disease in the list is actionable, and by clicking on it, the user may be driven to a web page describing the selected disease.

Figure 7:
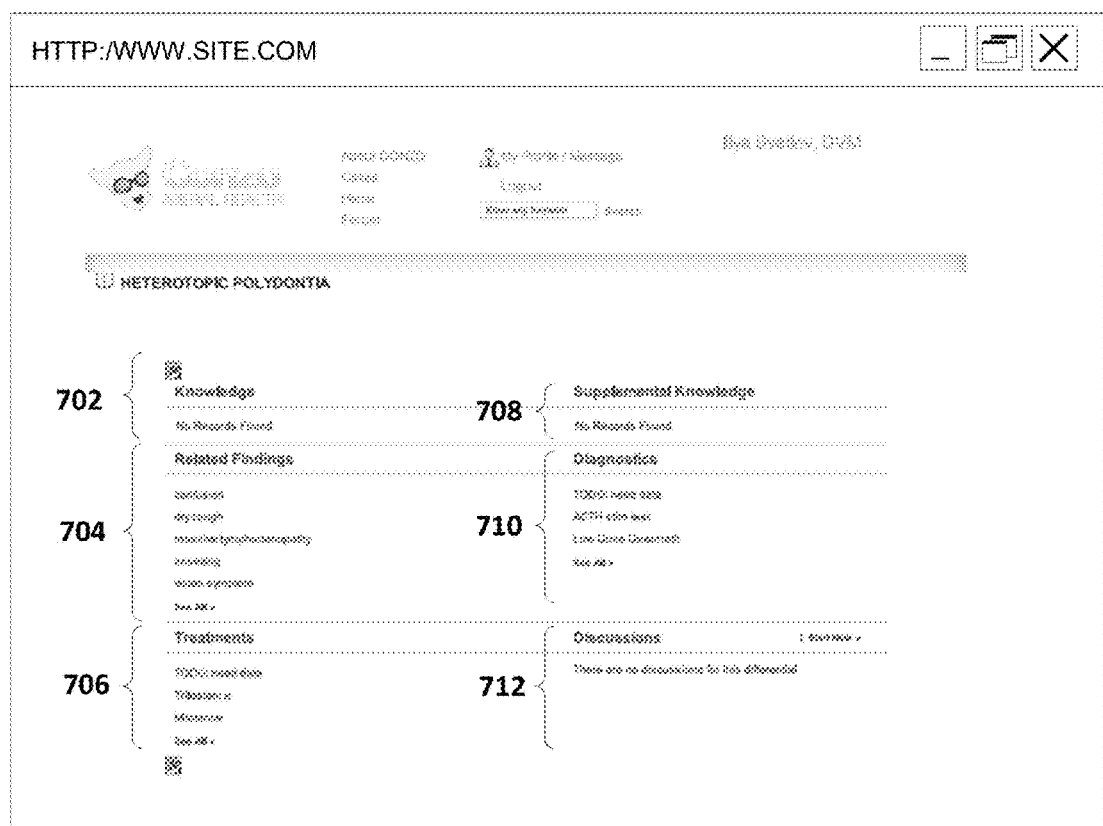
FIG. 7 is a simplified illustration of a graphical user interface of a web page related to an animal disease according to an example embodiment.

FIG. 7 is a simplified illustration of a graphical user interface 700 of a web page related to an animal disease according to an example embodiment. The graphical user interface 700 may be represented as a window (e.g., a browser window) to show its content. For example, the graphical user interface 700 may be presented on a screen of the client device 102 via the browser 110.

By way of example and not limitation, the graphical user interface 700 may comprise a section 702 to show information concerning a certain disease, a section 704 to show known clinical signs related to the disease, a section 706 to show known treatment methods, a section 708 to show supplementary knowledge related to the disease, a section 710 to show diagnostic methods related to examine the disease, and a section 712 to show discussions between different veterinary practitioners.

Those skilled in the art would appreciate that the graphical user interfaces 500, 600, 700 may comprise additional, fewer or other sections, widget or content.

Figure 8:
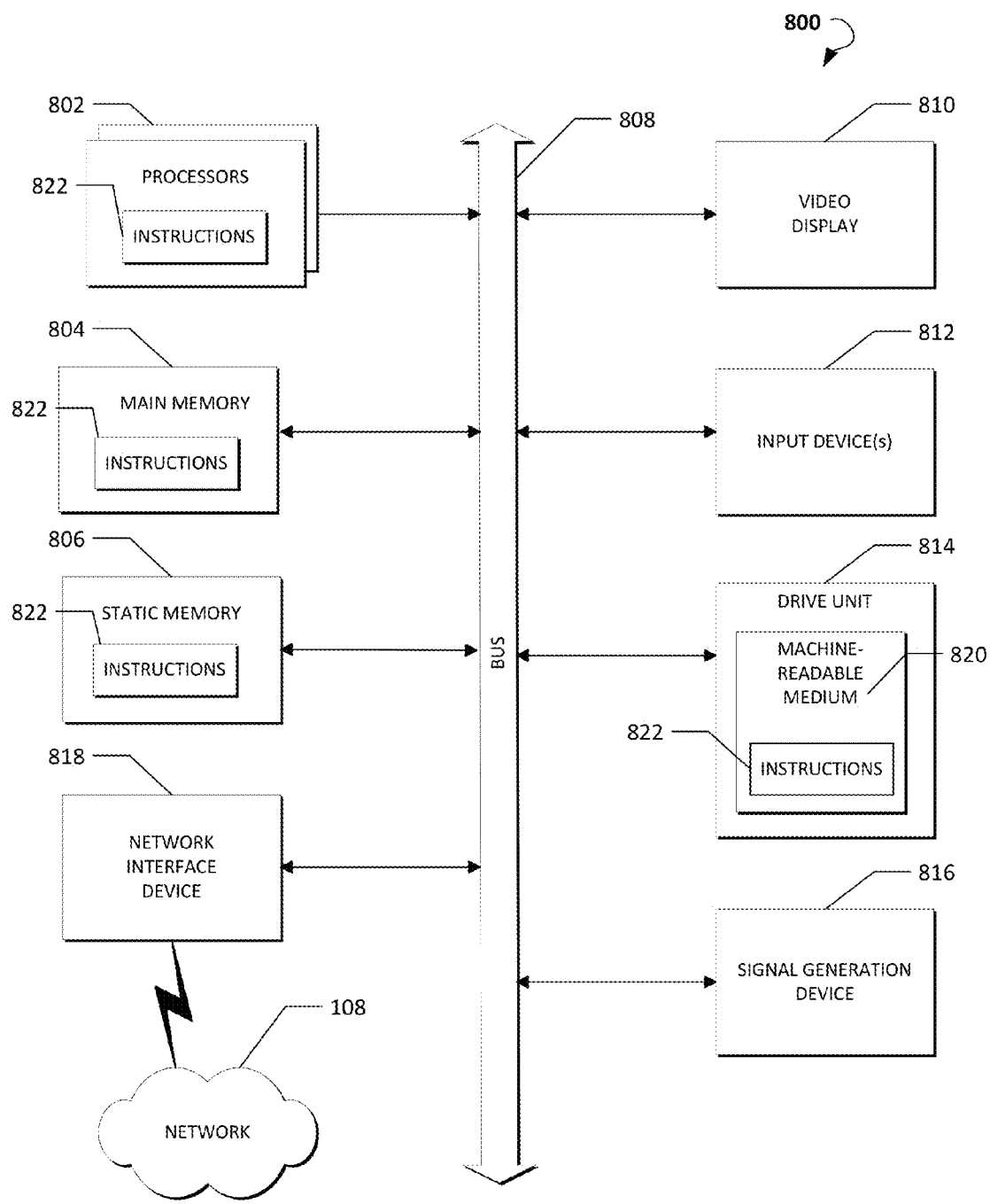
FIG. 8 is a diagrammatic representation of an example machine in the form of a computer system within which a set of instructions, for the machine to perform any one or more of the methodologies discussed herein, is executed.

FIG. 8 shows a diagrammatic representation of a computing device for a machine in the example electronic form of a computer system 800, within which a set of instructions for causing the machine to perform any one or more of the methodologies discussed herein can be executed. In various example embodiments, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a personal computer (PC), a tablet PC, a set-top box (STB), a PDA, a cellular telephone, a portable music player (e.g., a portable hard drive audio device, such as an Moving Picture Experts Group Audio Layer 3 (MP3) player), a web appliance, a network router, a switch, a bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 800 includes a processor or multiple processors 802 (e.g., a central processing unit (CPU), a graphics processing unit (GPU), or both), and a main memory 804 and a static memory 806, which communicate with each other via a bus 808. The computer system 800 can further include a video display unit 810 (e.g., a liquid crystal displays (LCD) or a cathode ray tube (CRT)). The computer system 800 also includes at least one input device 812, such as an alphanumeric input device (e.g., a keyboard), a cursor control device (e.g., a mouse), a microphone, a digital camera, a video camera, and so forth. The computer system 800 also includes a disk drive unit 814, a signal generation device 816 (e.g., a speaker), and a network interface device 818.

The disk drive unit 814 includes a computer-readable medium 820 which stores one or more sets of instructions and data structures (e.g., instructions 822) embodying or utilized by any one or more of the methodologies or functions described herein. The instructions 822 can also reside, completely or at least partially, within the main memory 804 and/or within the engines 802 during execution thereof by the computer system 800. The main memory 804 and the engines 802 also constitute machine-readable media.

The instructions 822 can further be transmitted or received over the network 108 via the network interface device 818 utilizing any one of a number of well-known transfer protocols (e.g., Hyper Text Transfer Protocol (HTTP), CAN, Serial, and Modbus).

While the computer-readable medium 820 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media. Such media can also include, without limitation, hard disks, floppy disks, flash memory cards, digital video disks, random access memory (RAMs), read only memory (ROMs), and the like.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software programs for implementing the present method can be written in any number of suitable programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Perl, UNIX Shell, Visual Basic or Visual Basic Script, Virtual Reality Markup Language (VRML), ColdFusion™ or other compilers, assemblers, interpreters or other computer languages or platforms.

Thus, computer-implemented method and systems for acquiring and processing information about non-human animal diseases are described. These methods and systems facilitate a computer-based differential diagnosis. Many studies demonstrated improvement of quality of care and reduction of medical errors by using such methods and systems.

Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A computer-implemented method for acquiring and processing information about non-human animal diseases, the method comprising:
   importing veterinary-related text information, wherein the veterinary-related text information is related to one or more non-human animal diseases;
   parsing the veterinary-related text information into one or more terms;
   determining relations between the one or more terms;
   classifying the one or more terms such that each term relates to one of: a non-human animal species, an animal disease, a medical sign and a treatment; and
   generating a database table associated with the imported veterinary-related text information, the database table comprising the one or more classified terms and the relations therebetween.

2. The method of claim 1, further comprising:
   selecting at least one predetermined ontology associated with the one or more terms, wherein the ontology has a structural framework of terms and relations therebetween.

3. The method of claim 2, wherein determining relations between the one or more terms is based on the structural framework of the at least one ontology.

4. The method of claim 2, wherein classifying the one or more terms is based on the structural framework of the at least one ontology.

5. The method of claim 1, wherein parsing the veterinary-related text information comprises applying predetermined semantic rules.

6. The method of claim 1, further comprising:
   assigning weight factors to the terms associated with the veterinary-related text information; and
   storing the weight coefficients in the table database.

7. The method of claim 1, wherein generating the database table associated with the imported veterinary-related text information comprises updating an existing database table.

8. The method of claim 1, further comprising:
   crawling one or more resources over a network to import the veterinary-related text information.

9. The method of claim 1, further comprising:
   generating, upon a user request, a web page related to a non-human animal disease, the web page comprising one or more of medical signs and treatments acquired from multiple resources.

10. The method of claim 1, further comprising:
    receiving a user request to conduct a veterinary differential diagnosis, wherein the user request comprises one or more of preselected medical signs;
    searching for information about non-human animal diseases, associated with the preselected medical signs, through the one or more database tables; and
    reporting the list of one or more non-human animal diseases.

11. The method of claim 10, further comprising:
    ranking the list of one or more non-human animal diseases based on the weight factors applied to the terms; and
    sorting the one or more non-human animal diseases on their relevancy.

12. The method of claim 1, further comprising:
    providing a user interface to access, search over, and process information about non-human animal diseases among the at least one database table.

13. The method of claim 1, further comprising:
    virtually linking the generated database table associated with the imported veterinary-related text information with one or more remote resources in the network.

14. The system of claim 1, further comprising:
    a user interface configured to enable users to access, search over, and process information about non-human animal diseases among the at least one database table.

15. A system for acquiring and processing information about non-human animal diseases, the system comprising:
    a communication module configured to import veterinary-related text information, wherein the veterinary-related text information comprises information related to one or more non-human animal diseases;
    a parsing module configured to parse the veterinary-related text information into one or more terms;
    a relationship determination module configured to determine relations between the one or more terms;
    a classifying module configured to classify the one or more terms such that each term relates to one of: a non-human animal species, an animal disease, a medical sign and a treatment; and
    a database table generator configured to generate a database table associated with the imported veterinary-related text information, the database table comprising the one or more classified terms and the relations therebetween.

16. The system of claim 15, further comprising:
    an ontology selecting module configured to select at least one predetermined ontology associated with the one or more terms, wherein the ontology has a structural framework of terms and relations therebetween.

17. The system of claim 15, further comprising:
    a ranking module configured to assign weight factors to the terms associated with the veterinary-related text information, and rank the list of one or more non-human animal diseases based on the weight factors applied to the terms.

18. The system of claim 15, further comprising:
    a crawling module configured to craw one or more resources over a network to import the veterinary-related text information.

19. The system of claim 15, further comprising:
a web page generator configured to generate, upon a user request, a web page related to a non-human animal disease, the web page comprising one or more of medical signs and treatments acquired from multiple resources.

20. A computer-readable medium having instructions stored thereon, which, when executed by one or more computers, cause the one or more computers to:
import veterinary-related text information, wherein the veterinary-related text information is related to one or more non-human animal diseases;
parse the veterinary-related text information into one or more terms;
determine relations between the one or more terms;
classify the one or more terms such that each term relates to one of: a non-human animal species, an animal disease, a medical sign and a treatment; and
generate a database table associated with the imported veterinary-related text information, the database table comprising the one or more classified terms and the relations therebetween.

* * * * *